United States Patent
Zanella, Sr.

(10) Patent No.: US 10,578,573 B2
(45) Date of Patent: Mar. 3, 2020

(54) DIAGNOSTICS FOR CATALYTIC STRUCTURES AND COMBUSTIBLE GAS SENSORS INCLUDING CATALYTIC STRUCTURES

(71) Applicant: Mark F. Zanella, Sr., Chicora, PA (US)

(72) Inventor: Mark F. Zanella, Sr., Chicora, PA (US)

(73) Assignee: MSA TECHNOLOGY, LLC, Cranberry Township, PA (US)

( * ) Notice: Subject to any disclaimer, the term of this patent is extended or adjusted under 35 U.S.C. 154(b) by 796 days.

(21) Appl. No.: 13/795,452

(22) Filed: Mar. 12, 2013

(65) Prior Publication Data

US 2014/0273263 A1 Sep. 18, 2014

(51) Int. Cl.
*G01N 27/16* (2006.01)

(52) U.S. Cl.
CPC .................................... *G01N 27/16* (2013.01)

(58) Field of Classification Search
CPC .. G01N 27/16; G01N 33/0031; G01N 33/007; G01N 25/20; G01N 25/22; G01N 25/32; G01N 33/225; Y10T 29/49004
See application file for complete search history.

(56) References Cited

U.S. PATENT DOCUMENTS

| | | | | |
|---|---|---|---|---|
| 3,484,773 A | * | 12/1969 | Archer et al. | G01N 27/16 340/633 |
| 3,593,126 A | * | 7/1971 | May | G01D 5/24 324/651 |
| 4,305,724 A | * | 12/1981 | Micko | G01N 27/16 422/94 |
| 4,314,475 A | | 2/1982 | Karpov | |
| 4,351,614 A | * | 9/1982 | Garnier | G01N 25/54 374/37 |
| 4,854,155 A | | 8/1989 | Poli | |
| 5,599,584 A | | 2/1997 | Champney, Jr. | |
| 5,780,715 A | * | 7/1998 | Imblum | G01N 33/0047 73/23.21 |

(Continued)

FOREIGN PATENT DOCUMENTS

| | | |
|---|---|---|
| EP | 1480035 A2 | 11/2004 |
| WO | WO2011053866 A1 | 5/2011 |

OTHER PUBLICATIONS

Fu et al. "Using Reactance Measurement Way to Improve the Selectivity of SnO2 Gas Sensors", CNKI. Instrument Technique and Sensor, Feb. 2001, Abstract.*

(Continued)

*Primary Examiner* — Robert J Eom
(74) *Attorney, Agent, or Firm* — Bartony & Associates, LLC

(57) ABSTRACT

A combustible gas sensor for detecting a combustible analyte includes a first sensing element including a first conductive element in electrical connection with an electronic circuitry, a first support structure in operative connection with the first conductive element, a catalyst supported on the first support structure for catalyzing a reaction of the analyte, and a system for measuring a variable related to the reactance of the first sensing element. Changes in the measured variable over time provide an indication of an operational status of the first sensing element.

18 Claims, 7 Drawing Sheets

(56) References Cited

U.S. PATENT DOCUMENTS

| | | | |
|---|---|---|---|
| 6,705,152 | B2 | 3/2004 | Routkevitch |
| 7,413,645 | B2 | 8/2008 | Scheffler |
| 2002/0146352 | A1 | 10/2002 | Wang |
| 2006/0289400 | A1 | 12/2006 | Takahashi |
| 2011/0100090 | A1 | 5/2011 | Zanella, Sr. |

OTHER PUBLICATIONS

"Inductive and Capacitive Reactance", Mar. 2016 (http://www.sayedsaad.com/fundmental/15_INDUCTIVE%20AND%20CAPACITIVE%20REACTANCE%20.htm).*

Krawczyk, Mariusz, and J. Namiesnik. "Application of a catalytic combustion sensor (pellistor) for the monitoring of the explosiveness of a hydrogen-air mixture in the upper explosive limit range." Journal of Analytical Methods in Chemistry 25.5 (1900): 115-122.*

International Search Report and Written Opinion of counterpart International PCT application No. PCT/US2014/21753 filed on Mar. 7, 2014.

Mosely, P.T. and Tofield, B.C., ed., Solid State Gas Sensors, Adams Hilger Press, Bristol, England, 17-31, (1987).

Firth, J.G. et al., Combustion and Flame, 21, 303-311, (1973).

Cullis, C.F., and Firth, J.G., Eds., Detection and Measurement of Hazardous Gases, Heinemann, Exeter, 29-67, (1981).

Baxter, L. K., Capacitive Sensors, White Paper, (2000), 1-17.

\* cited by examiner

DIAGNOSTICS FOR CATALYTIC STRUCTURES AND COMBUSTIBLE GAS SENSORS INCLUDING CATALYTIC STRUCTURES

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Catalytic or combustible (flammable) gas sensors have been in use for many years to, for example, prevent accidents caused by the explosion of combustible or flammable gases. In general, combustible gas sensors operate by catalytic oxidation of combustible gases. As illustrated in FIGS. 1A and 1B, a conventional combustible gas sensor 10 typically includes an element such as a platinum heating element wire or coil 20 encased in a refractory (for example, alumina) bead 30, which is impregnated with a catalyst (for example, palladium or platinum) to form an active or sensing element, which is sometimes referred to as a pelement 40, pellistor, detector or sensing element. A detailed discussion of pelements and catalytic combustible gas sensors which include such pelements is found in Mosely, P. T. and Tofield, B. C., ed., *Solid State Gas Sensors*, Adams Hilger Press, Bristol, England (1987). Combustible gas sensors are also discussed generally in Firth, J. G. et al., *Combustion and Flame* 21, 303 (1973) and in Cullis, C. F., and Firth, J. G., Eds., *Detection and Measurement of Hazardous Gases*, Heinemann, Exeter, 29 (1981).

Bead 30 will react to phenomena other than catalytic oxidation that can change its output (i.e., anything that changes the energy balance on the bead) and thereby create errors in the measurement of combustible gas concentration. Among these phenomena are changes in ambient temperature, humidity, and pressure.

To minimize the impact of secondary effects on sensor output, the rate of oxidation of the combustible gas may be measured in terms of the variation in resistance of sensing element or pelement 40 relative to a reference resistance embodied in an inactive, compensating element or pelement 50. The two resistances are typically part of a measurement circuit such as a Wheatstone bridge circuit as illustrated in FIG. 1C. The output or the voltage developed across the bridge circuit when a combustible gas is present provides a measure of the concentration of the combustible gas. The characteristics of compensating pelement 50 are typically matched as closely as possible with active or sensing pelement 40. Compensating pelement 50, however, typically either carries no catalyst or carries an inactivated/poisoned catalyst.

Active or sensing pelement 40 and compensating pelement 50 can, for example, be deployed within wells 60a and 60b of an explosion-proof housing 70 and can be separated from the surrounding environment by a flashback arrestor, for example, a porous metal frit 80. Porous metal frit 80 allows ambient gases to pass into housing 70 but prevents ignition of flammable gas in the surrounding environment by the hot elements. Such catalytic gas sensors are usually mounted in instruments which, in some cases, must be portable and, therefore, carry their own power supply. It is, therefore, desirable to minimize the power consumption of a catalytic gas sensor.

Catalytic combustible gas sensors are typically used for long periods of time over which deterioration of the sensing element or the like and malfunction of circuits may occur. A foreign material such as an inhibiting material or a poisoning material (that is, inhibiting or poisoning of the catalyst of the sensing element) may, for example, be introduced to the sensing element. An inhibiting material typically will "burn off" over time, but a poisoning material permanently destroys catalytic activity of the sensing element. In general, it is difficult to determine such an abnormal operational state or status of a combustible gas sensor without knowingly applying a test gas to the combustible gas sensor. In many cases, a detectible concentration of a combustible gas analyte in the ambient environment is a rare occurrence. Testing of the operational status of a combustible gas sensor typically includes the application of a test gas (for example, a gas including a known concentration of the analyte or a simulant thereof to which the combustible gas sensor is similarly responsive) to the sensor. Periodic testing using a combustible gas may be difficult, time consuming and expensive.

For decades sensor designers have been perplexed with the problems of contamination and/or degradation of their catalyst structures. Sulfur compounds (inhibitors) have been known to inhibit the catalyst structures, and filtering techniques are used to prevent their passage into the structure. If they do enter the structure, they are bound until a sufficient level of heat is applied to promote their release or decomposition. Volatile silicon compounds (poisons) are also known to cause significant issues with catalytic structures as they are permanently retained, and eventually result in the total inactivity of the catalyst. Finally, high levels of hydrocarbons can also deposit incomplete and/or secondary byproducts such as carbon within the structure.

All of these issues go undetected by the high sensitivity bridge circuits used over the years in combustible gas sensors. Users have long reported cases where their catalytic sensors are reading zero (that is, the bridge circuitry is balanced), yet they show little response to gas challenges. A number of sweeping, ramping and pulsing techniques have been attempted to detect minute changes in the thermodynamic properties of the sensing elements. However such techniques are only partially effective when large scale changes have occurred. Moreover, the sensors have to be taken off-line for analysis to use these techniques, potentially missing a dangerous safety event.

SUMMARY

In one aspect, a combustible gas sensor for detecting a combustible analyte includes a first sensing element including a first conductive element in electrical connection with an electronic circuit, a first support structure in operative connection with the first conductive element, a catalyst supported on the first support structure for catalyzing a reaction of the analyte, and a system for measuring a variable related to the complex component of impedance, which is sometimes referred to as reactance, of the first sensing element (variables that may be measured include, but are not limited to, impedance, reactance, resonant frequency, a frequency dependent variable, inductance, capacitance, or the reactive components of inductance and/or capacitance). Changes in the measured variable over time provide an indication of an operational status of the first sensing element.

Impedance is defined by the formula $Z=R+jX$, wherein Z is the impedance. The real component of impedance Z is the resistance R, while the complex or imaginary component of impedance is the reactance X (wherein j is the imaginary unit). Both capacitive reactance $X_C$ and the inductive reactance $X_L$ contribute to reactance (or total reactance) according to the following formula $X=X_L-X_C$. In general, measurement of impedance or reactance (and/or variables related thereto) requires a variation in applied voltage or current. In the absence of an analyte, resistance of the sensing element remains constant over time, but the complex component of impedance (that is, reactance) varies as a function of sensing element operational state or functionality as described herein.

The first conductive element may, for example, pass through at least a portion of the first support structure. In a number of embodiments, the combustible gas sensor is operative to detect the combustible gas analyte during the measurement of a variable related to the reactance of the first sensing element. More than one variable related to reactance may, for example, be measured.

In a number of embodiments, the combustible gas sensor further includes a compensating element including a second conductive element in electrical connection with the electronic circuit and a second support structure in operative connection with the second conductive element. The compensating element is substantially non-reactive with the combustible analyte at a temperature of operation of the compensating element.

The first support structure may, for example, include a porous, electrically insulating material. The first support structure may, for example, include a porous refractory material.

A change in the measured variable may, for example, provide an indication of a foreign material being introduced to the first sensing element. The foreign material may, for example, be an inhibitor or a poison.

The combustible gas sensor may, for example, further include a control system in communicative connection with the electronic circuitry. The control system may, for example, be adapted to alter the output of the combustible gas sensor based on a change in the measured variable. Such alterations and other actions performed by the control system may, for example, be automated (that is, not require user intervention). The control system may also be adapted to provide information to a user regarding the operational status of the first sensing element based on a change in the measured variable. In a number of embodiments, the control system may also be adapted to increase the temperature of the first sensing element upon the change in the measured variable related to reactance to attempt to burn off the foreign material. The control system may also be adapted to provide an indication to a user in the case that the measured variable (and/or sensitivity of the sensing element) fails to return to a predetermined threshold as a result of the increase in temperature.

In a number of embodiments, the system for measuring the variable related to reactance measures at least one of the impedance of the first sensing element, the reactance of the first sensing element, the inductance of the first sensing element, the capacitance of the first sensing element, the reactive components of inductance and/or capacitance of the first sensing element, the resonant frequency of the first sensing element, or a frequency dependent variable of the first sensing element.

In another aspect, a method of operating a combustible gas sensor for detecting a combustible analyte is provided. The combustible gas sensor includes a first sensing element having a first conductive element in electrical connection with electronic circuitry, a first support structure in operative connection with the first conductive element, and a catalyst supported on the first support structure for catalyzing a reaction of the analyte. The method includes measuring a variable related to reactance of the first sensing element as described above over time and relating changes in the measured variable to an operational state of the first sensing element. In a number of embodiments, the combustible gas sensor is operative to detect the combustible gas analyte while the variable related to reactance of the first sensing element is measured.

In a further aspect, a method of determining the operational status of a sensing element including a conductive element in electrical connection with an electronic circuit, a support structure in operative connection with the first conductive element, and a catalyst supported on the support structure for catalyzing a reaction of the analyte, includes measuring a variable related to reactance of the sensing element over time and relating changes in the measured variable to the operational state of the sensing element.

In still a further aspect, a method is provided of operating a combustible gas sensor for detecting a combustible analyte gas. The combustible gas sensor includes a first sensing element having a first conductive element in electrical connection with an electronic circuit, a first support structure in operative connection with the first conductive element, and a catalyst supported on the first support structure for catalyzing a reaction of the analyte. The combustible gas sensor further includes a control system in operative connection with the first sensing element. The method includes electronically interrogating the sensing element via the control system without applying the analyte gas or a simulant therefor to the first sensing element to test an operational state of the first sensing element and increasing the temperature of the first sensing element via the control system upon determining from the electronic interrogation that a foreign material has contaminated the first sensing element to attempt to burn off the foreign material. The method may, for example, further include repeating the electronic interrogation to determine whether the foreign material has been removed to a sufficient degree. The method may, for example, further include providing an indication to a user of a failure to remove the foreign material to the sufficient degree.

In a number of embodiments, the electronic interrogation includes measuring a variable related to reactance of the sensing element over time and relating changes in the measured variable to the operational state of the sensing element. The system for measuring the variable may, for example, measure at least one of the impedance of the first sensing element, the reactance of the first sensing element, the inductance of the first sensing element, the capacitance of the first sensing element, the reactive components of the inductance and/or capacitance of the first sensing element, the resonant frequency of the first sensing element, or a the frequency dependent variable of the first sensing element. In a number of embodiments, the combustible gas sensor is operative to detect the combustible gas analyte while the variable related to reactance of the first sensing element is measured.

Devices, systems and/or methods described herein, along with the attributes and attendant advantages thereof, will best be appreciated and understood in view of the following detailed description taken in conjunction with the accompanying drawings.

DETAILED DESCRIPTION

Figure 1B:
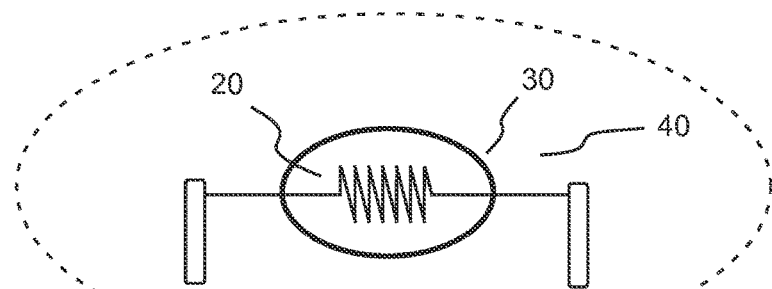
FIG. 1B illustrates an enlarged view of the active sensing element, pelement or detector of the combustible gas sensor of FIG. 1A.
Figure 1A:
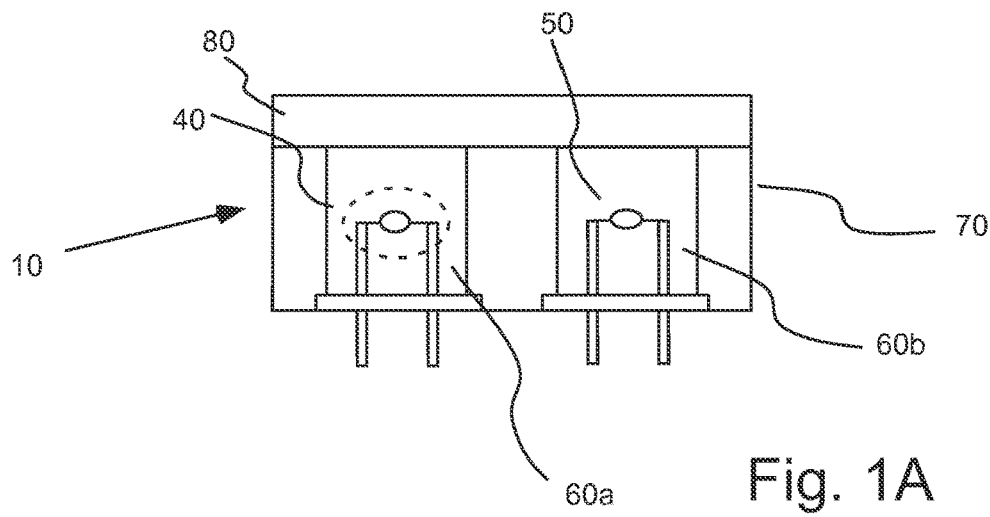
FIG. 1A illustrates an embodiment of a currently available combustible gas sensor.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a sensing element" includes a plurality of such sensing element and equivalents thereof known to those skilled in the art, and so forth, and reference to "the sensing element" is a reference to one or more such sensing elements and equivalents thereof known to those skilled in the art, and so forth.

In a number of embodiments hereof, devices, systems and method of determining the well-being or operational status of a catalytic structure (for example, a sensing element in a combustible gas sensor) are set forth that do not require the use or application of the analyte (or target) gas or a simulant thereof (that is, the application of a test gas is not required). The catalytic structures generally include a heating element (typically a conductive element), an insulating catalyst support structure disposed on the heating element, and a catalyst disposed upon the support structure. In a number of embodiments, reactance testing methods are used to measure a variable related to reactance to interrogate/determine the operational state or functionality of the catalytic structure/sensing element. The term "variable related to reactance" refers to a variable that varies with or is proportional to the reactance (or the complex component impedance) including, for example, impedance, reactance, inductance, capacitance, the reactive components of inductance and/or capacitance, resonant frequency, or a frequency dependent variable. One or more such variables are measured over time and changes therein are related to the operational state or functionality of the catalytic structure/sensing element. In general, reactance provides a measurement of the opposition of a circuit element to a change of electric current or voltage, as a result of that element's inductance or capacitance. In a number of embodiments, either reactive components or reactive components of inductance and/or capacitance may be measured. Alternatively or additionally, other variables related to inductance and/or capacitance, such as resonant frequency, may be measured. Still other variables such as the variation in amplitude of the application of a fixed frequency may be measured. Further, another variable such as determined by a frequency or phase comparison of the devices resonant frequency to a fixed reference frequency may be measured.

In a number of representative studies set forth herein, capacitance or a variable related to capacitance is measured. However, one skilled in the art appreciates that any variable related to reactance (and changes therein) may be measured. Such variables may, for example, be related to or indicative of the presence of a contaminant on the catalytic structure of a sensing element and/or to the sensitivity of a sensing element for an analyte.

Figure 2A:
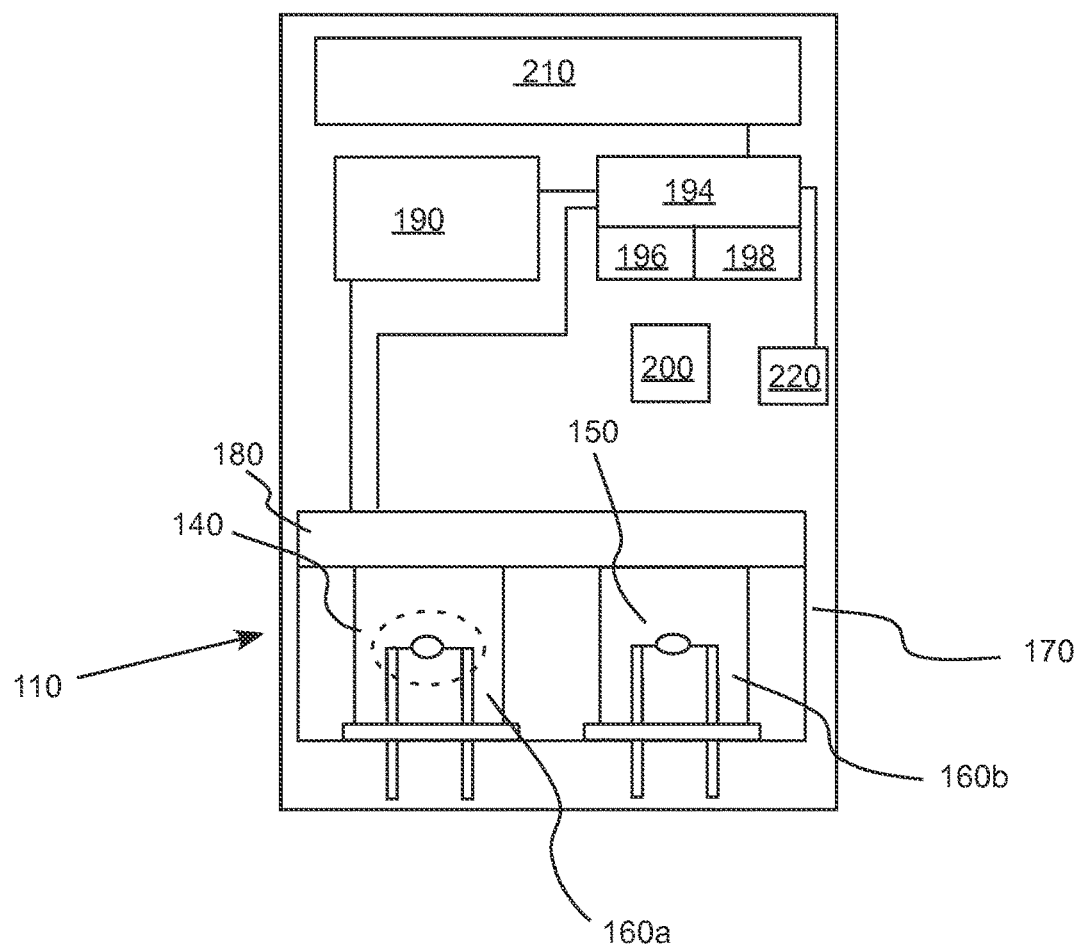
FIG. 2A illustrates an embodiment of a combustible gas sensor system hereof including a system to measure a variable related to reactance of an active sensing element thereof.

FIG. 2A illustrates an embodiment of a combustible gas sensor 110 hereof. As described above for sensor 10, combustible gas sensor 110 includes, for example, an active or sensing element (or pelement) 140 and a compensating element 150 Active sensing element 140 and compensating element 150 are disposed within wells 160a and 160b, respectively, of an explosion-proof housing 170. Active or sensing element 140 and compensating element 150 are separated from the surrounding environment by a flashback arrestor (for example, a porous metal frit 180). Porous metal frit 180 allows ambient gases to pass into housing 70 but prevents ignition of flammable gas in the surrounding environment by the hot elements. Catalytic combustible gas sensor 110 is, for example, mounted within a system or instrument which may be portable or fixed in position (that is, permanent). The system or instrument may, for example, include a single combustible gas sensor or multiple combustible gas sensors. In the case of multiple combustible gas sensors, interrogations or tests as described herein may be performed on each combustible gas sensor. Other sensors such as electrochemical gas sensors may also be present in the instrument or system.

A power source 190 is in operative connection with sensor 110. In the case of a sensor fixed at a position within a facility, power may be provided from a remote source. In the case of a portable sensor, power source 190 may include one or more batteries. Sensor 110 also includes a control system 194 which may, for example, include control circuitry and/or a processor 196 (for example, a microprocessor) and an associated memory system 198 in communicative connection with processor 196.

Figure 1C:
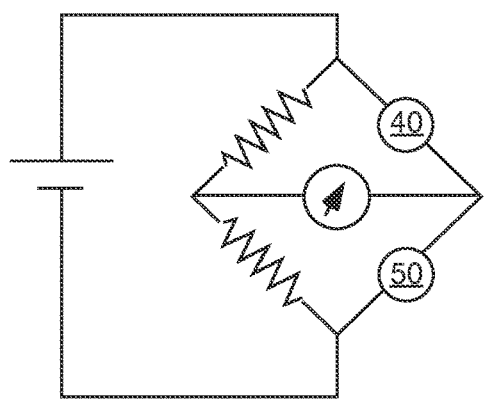
FIG. 1C illustrates an embodiment of the circuitry of the combustible gas sensor of FIG. 1A.
Figure 2B:
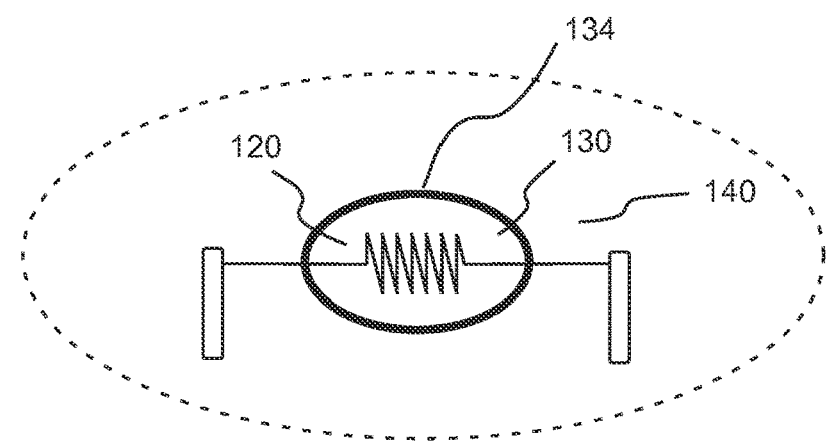
FIG. 2B illustrates an enlarged view of the active sensing element of the combustible gas sensor system of FIG. 2A.

A heating element 120 (FIG. 2B) such as a conductive wire is used to sufficiently raise the temperature of the structure of the element (including support structure 130 and catalyst 134) to a temperature to promote the catalytic reaction of the analyte or target gas. Heating elements have generally been made from coils, and over time smaller diameter wires have been used to reduce the power consumption of the element. The use of small-diameter wires in combustible gas sensor are, for example, disclosed US Published Patent Application No. 2011/0100090, the disclosure of which is incorporated herein by reference. In general, wires for heating elements are selected to have a favorable temperature coefficient for sensing applications and are generally a precious metal or alloy. Active element 140 and compensating element 150 may, for example, be configured in some form of bridge circuit (as, for example, illustrated in FIG. 1C), and are operated at a constant voltage, current or resistance (and thereby at a constant temperature).

Insulating support structure 130 is generally formed to encapsulate heating element 120 and to promote good heat distribution. It is also desirable for support structure 140 to be very porous so that as many catalytic sites as possible can be formed thereon. A common suspension chosen is aluminum oxide, which is also an insulator and has a dielectric constant in the range of 3-5.

Catalyst 134 may, for example, be fired onto support structure 130 (for example, aluminum oxide). As described above, catalyst 134 may, for example, be a precious metal, such as platinum, palladium, rhodium or a mixture of metals. Catalyst 134 may, for example, be added to support structure 130 until (metallic) catalyst 134 begins to have an adverse effect on the impedance of heating element 120. Maximizing the catalyst material deposited maximizes the catalytic reaction and produces as much signal as possible. A complex, three dimensional metal and ceramic structure is formed with sufficient porosity to permit gas diffusion into the structure.

Figure 3:
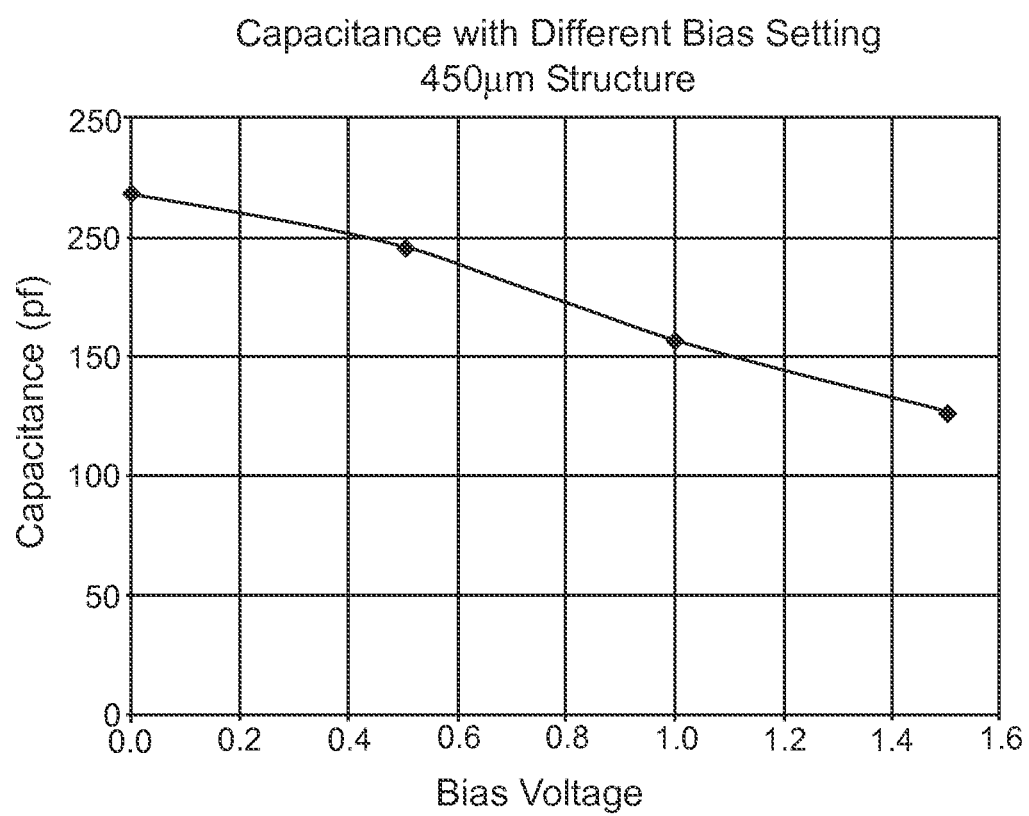
FIG. 3 illustrates a study of the effect of temperature upon the active sensing element.

Without limitation to any mechanism, it was theorized by the inventor that the catalyst structure may be modeled as a complex formation of intermingled metallic plates with electrical insulators and air therebetween. In its simplest form, this describes a basic capacitive structure. Analysis was conducted, and it was discovered that a representative 450 μm diameter semi-spherical catalytic structure had a capacitance of approximately 100 pf to 200 pf at 100 kHz as determined using an LCR meter. It was further confirmed by the application of a bias potential to the element. As the element is heated (biased), thermal expansion of the catalytic structure occurs. This thermal expansion causes the capacitive plates to separate, and a decrease in capacitance can be measured as illustrated in FIG. 3. This is consistent with the general capacitive equation of $C=\varepsilon A/d$, where d is the plate separation, A is area of overlap between two plates and $\varepsilon$ is the dielectric constant for the material in the gap that separates the plates. In a number of embodiments of system 110, sensing element 140 is operated at constant temperature to sense the analyte such that the effects of temperature on capacitance thereof do not affect operation.

As described above, the problems of contamination and/or degradation of catalyst structures has perplexed those in the art for years. Once again, sulfur compounds are known to inhibit the catalyst structures, and are bound until a sufficient level of heat is applied to promote their release or decomposition. Silicon compounds, however, are permanently retained and result in the total inactivity of the catalyst. Also, hydrocarbons can also deposit incomplete and/or secondary byproducts such as carbon within the structure. Sulfur, silica and carbon have dielectric constants in the range of 3-5.

An investigation conducted by the inventor demonstrated that the theorized labyrinth of capacitive elements can be used to measure the introduction of inhibiting or poisoning material into a catalyst structure such a sensing element 140. Since the air within the structure is displaced by materials of differing dielectrics, a measurable and tangible result is observed. Furthermore, the system may be interrogated to measure change in capacitance (or other variable related to reactance) while still performing its primary gas detection function.

Figure 4:
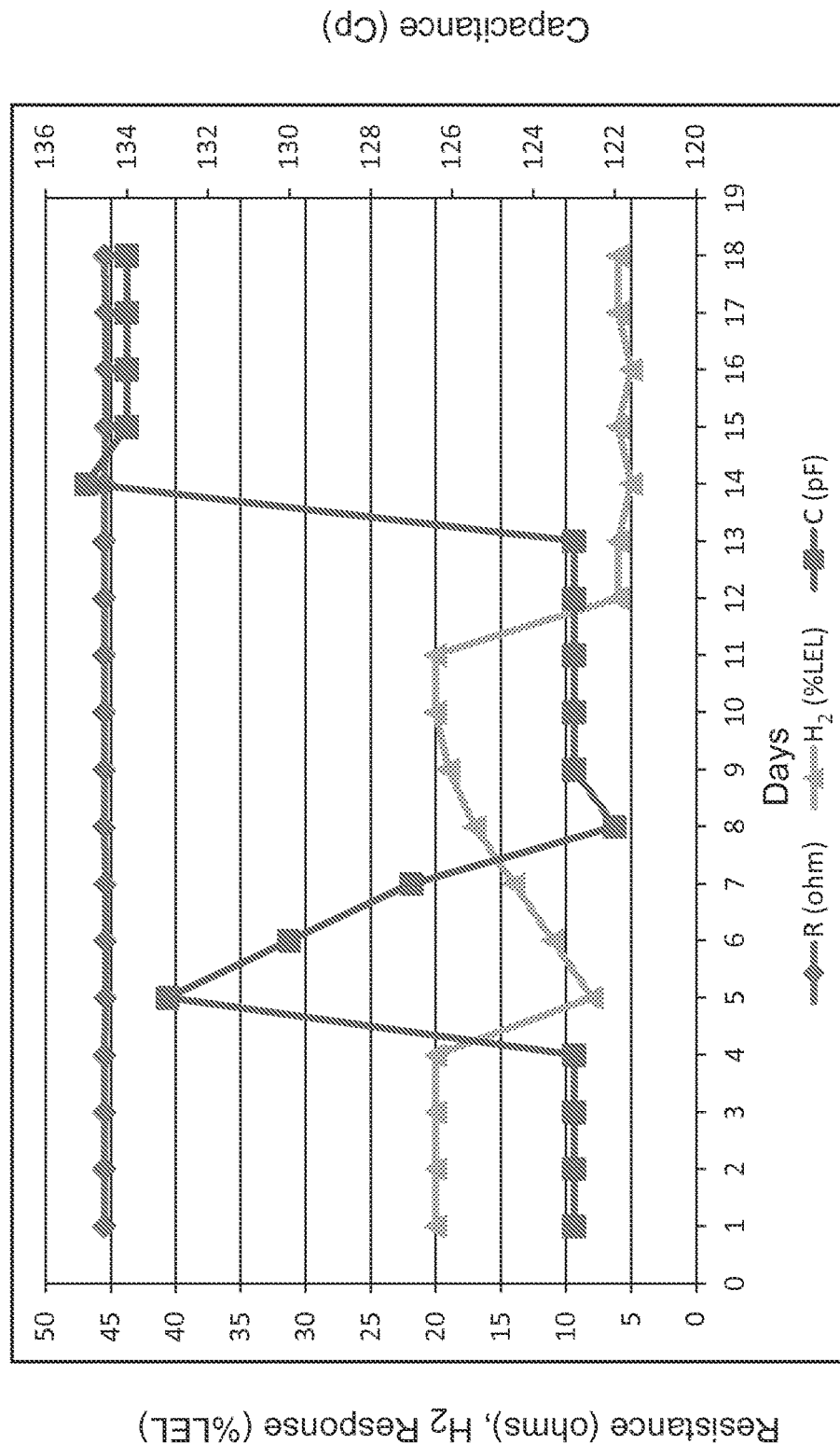
FIG. 4 illustrates the effect of the introduction of an inhibitor (sulfur) upon the resistance, capacitance and hydrogen sensitivity of an active sensing element for the detection of hydrogen.

FIG. 4 illustrates the result of testing a 450 um catalytic structure biased at IV with an Agilent 4263B LCR Meter. Initially, daily checks were performed, indicating that a stable response to $H_2$ was present, as well as stable resistance (R) and capacitance (C) readings, which were taken without the application of $H_2$. On day 5, the sulfur (in the form of a drop of 2.2N sulfuric acid) was applied to the catalytic structure (or catalytic pelement). The application of sulfuric acid resulted in a 60% decrease in $H_2$ response and a measurable change in capacitance. The resistance on the other hand did not change, which is consistent with user findings in previously available system. Over the course of the next 6 days, a slow recovery in gas sensitivity from the sulfur inhibition occurred. One can see from FIG. 4, the capacitance also slowly recovered, and was representative of the return to full gas sensitivity. The resistance remained unaffected throughout the study. An application with silica in the form of a drop of hexamethyldisiloxane (HDMS) was applied on day 14 and showed shifts similar to those occurring with application of sulfur in the form of sulfuric acid. However, neither the gas sensitivity nor the capacitance recovered after application of the silica poison, while again the resistance remained unchanged.

As conventional capacitive theory suggests, the introduction of a material (for example, sulfur) with a dielectric constant $\varepsilon$ higher than the air that is replaced thereby results in a capacitive increase. As described above, one skilled in the art can also appreciate that other variables related to the complex component of impedance or reactance may also be analyzed. Some of these analysis methods may result in an increase or decrease in the measured shift (that is, a variable related to reactance may go up or down). As described above, a reactive and/or resistive component of inductance and/or capacitance may be analyzed. Additionally, an approach which determines the resonant frequency of the reactive component of the catalyst structure may also be employed. The shift in resonance may be analyzed as an alternative method. Furthermore, one may analyze the amplitude of the application of a fixed frequency. The change is amplitude would be an indication of the change in the impedance. Still further, the resonant or natural frequency of the device may be compared to a secondary reference frequency. These two signals may then be compared for changes in phase as an indication of the change in the impedance. Another simple method would use the application of a voltage or current to the device and allow it to reach a steady state. The time required would be analyzed as a method of determining the impedance/reactance.

To implement the devices, systems and methods hereof, one skilled in the art needs simply, for example, to interrogate or measure the capacitance of a catalytic structure such as sensing element 140 as a capacitive sensor. A shift in capacitance for a given bias potential (that is, for a given temperature) indicates that the catalytic structure has been affected. An application circuit or system for measuring capacitance is represented schematically as system 200 in FIG. 2A. Suitable application circuits or systems for such an interrogation or capacitance measurement are numerous, and many of the applicable systems for sensing changes in capacitance are described, for example, Baxter, L. K., Capacitive Sensors: Design and Applications, IEEE Press (1997) as well as Baxter, L. K., Capacitive Sensors, White Paper, (2000), the disclosures of which are incorporated herein by reference.

Figure 5:
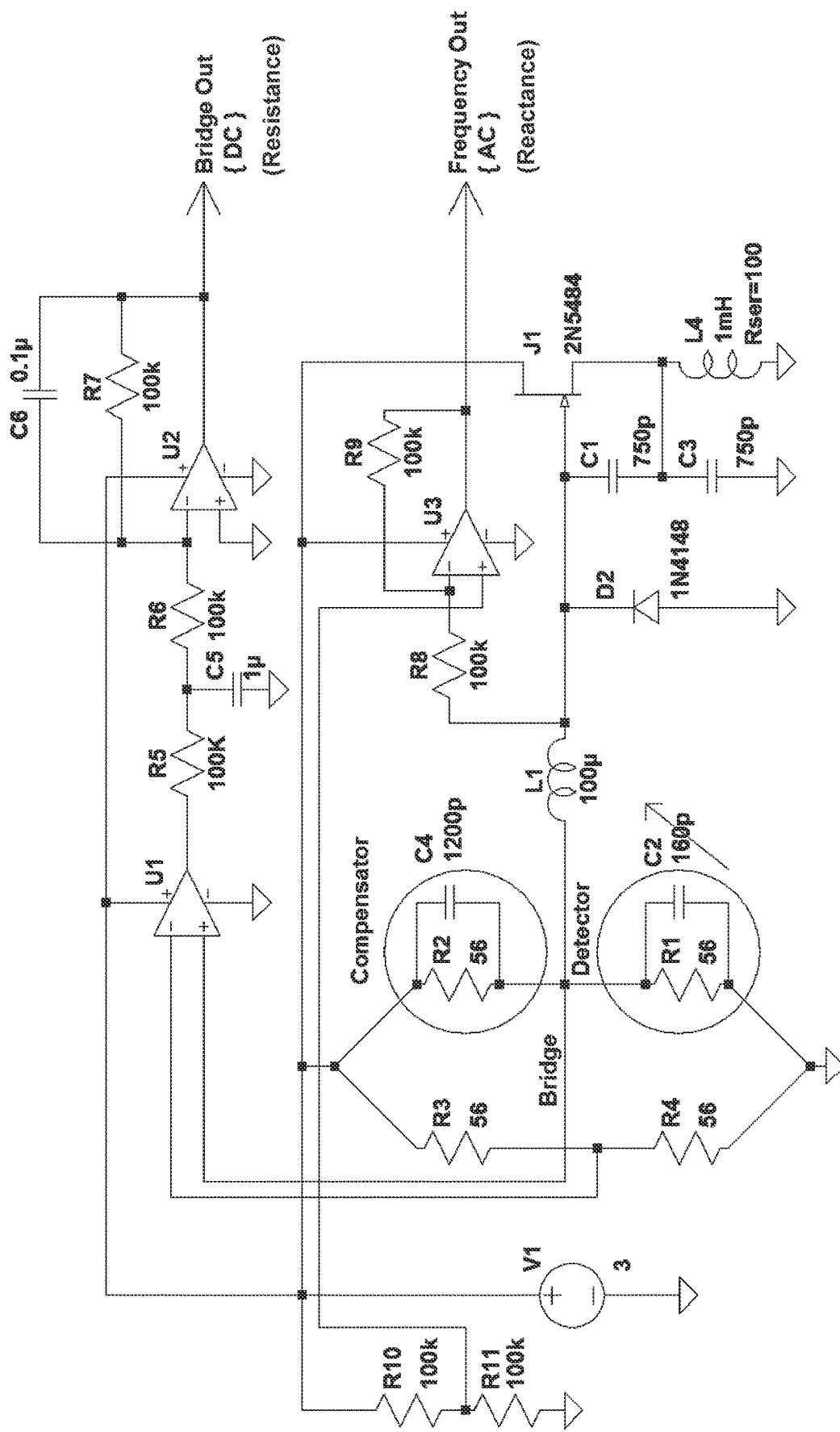
FIG. 5 illustrates a circuit diagram of one embodiment of a system to measure changes in the DC resistance as well as the reactance, as related to its resonant frequency, of an active sensing element.
Figure 6:
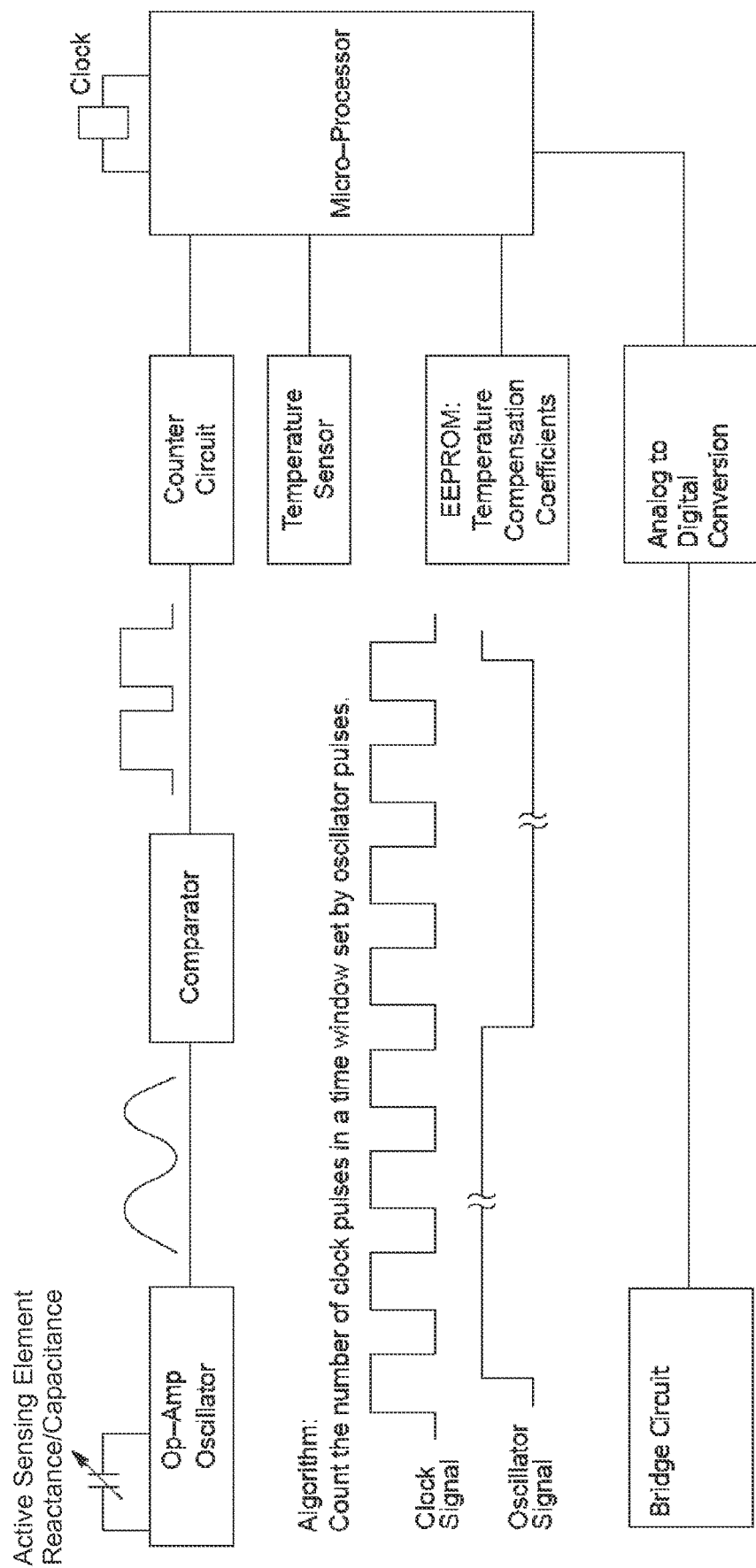
FIG. 6 illustrates a block diagram of an embodiment of a system hereof in which reactance/capacitance of an active sensing element of a combustible gas is monitored.

FIG. 5 illustrates a circuit diagram of a representative embodiment of a system used to measure changes in a variable related to reactance (for example, capacitance) of an active sensing element (Detector). In the system of FIG. 5, the bridge circuit (via amplifiers U1 and U2) provided a measurement of the gas concentration (Bridge Out), which is also a measure of the real or resistive component of the impedance. A Clapp Oscillator measures the bead capacitance (C2) as it relates to its resonant frequency whereas frequency=$1/[2\Pi(L1*C2)^{1/2}]$. This portion of the measurement system is a variable related to the complex or reactive component of the impedance. FIG. 6 illustrates a block diagram of the system.

There are many potential applications for the relationship between the complex component of impedance or reactance and the operational state of a catalyst structure described herein. For example, the measured variable may simply be used to provide an indication of the operational state of the sensor health, the sensor life (via, for example, a display system 210 and/or an alarm system 220) and/or just a diagnostic check in general.

In another application, the measured variable may be used to correct gas concentration output/readings in real-time. Below is a representative example of a formula for adjusting the sensitivity of the system.

$$S_t = S_o * (Y_o / Y_t * k)$$

In the above equation, $S_t$ is the sensitivity at a given time t; $S_o$ is the initial or previously determined sensitivity, $Y_o$ is the initial or previously determined variable related to reactance, $Y_t$ is the variable measured at a given time t and k is a scaling factor constant. A lookup table may, for example, alternatively be used to related a change in the measured variable to a sensitivity correction.

Unlike prior methodologies for measuring sensor operational state, interrogation of the sensing element can occur in the devices, systems and methods hereof without the disruption of the gas sensing function. This is a highly desirable ability. In that regard, a dangerous level of an analyte gas may arise during any time that the gas sensing function of a sensing element is disrupted. Preventing disruption of the gas sensing function of a sensing element (or providing for continuous sensing as long as the sensing element is operable to detect the analyte gas) improves the safety of the system.

Furthermore, a measured variable related to reactance could be used as a trigger to apply additional heat to the catalyst structure to potentially remove inhibitors. Periodic measurement of the variable, analysis of the results thereof, correction of sensor output and/or application of additional heat may, for example, be effected by control system 194 (via, for example, an algorithm or algorithms stored in memory system 198 as software) in an automated manner without user intervention. The measurement of a variable related to reactance and associated application of additional heat may be done in real time and offer not only a life and health aspect for the system, but a self-curing attribute. A sensor system including the ability to test and maintain its own health is a significant improvement in the art. Moreover, if the sensor fails to "burn off" a contaminant, it can be determined that the contaminant is a poison. The user may be notified that the active element of the system has been poisoned (for example, via display system 210, alarm system 220 and/or other user interfaces). The "burn off" procedure described herein may, for example, be used in connection with any electronic interrogation of the active sensing element that is suitable to determine that a foreign material has contaminated the active sensing element.

Figure 7:
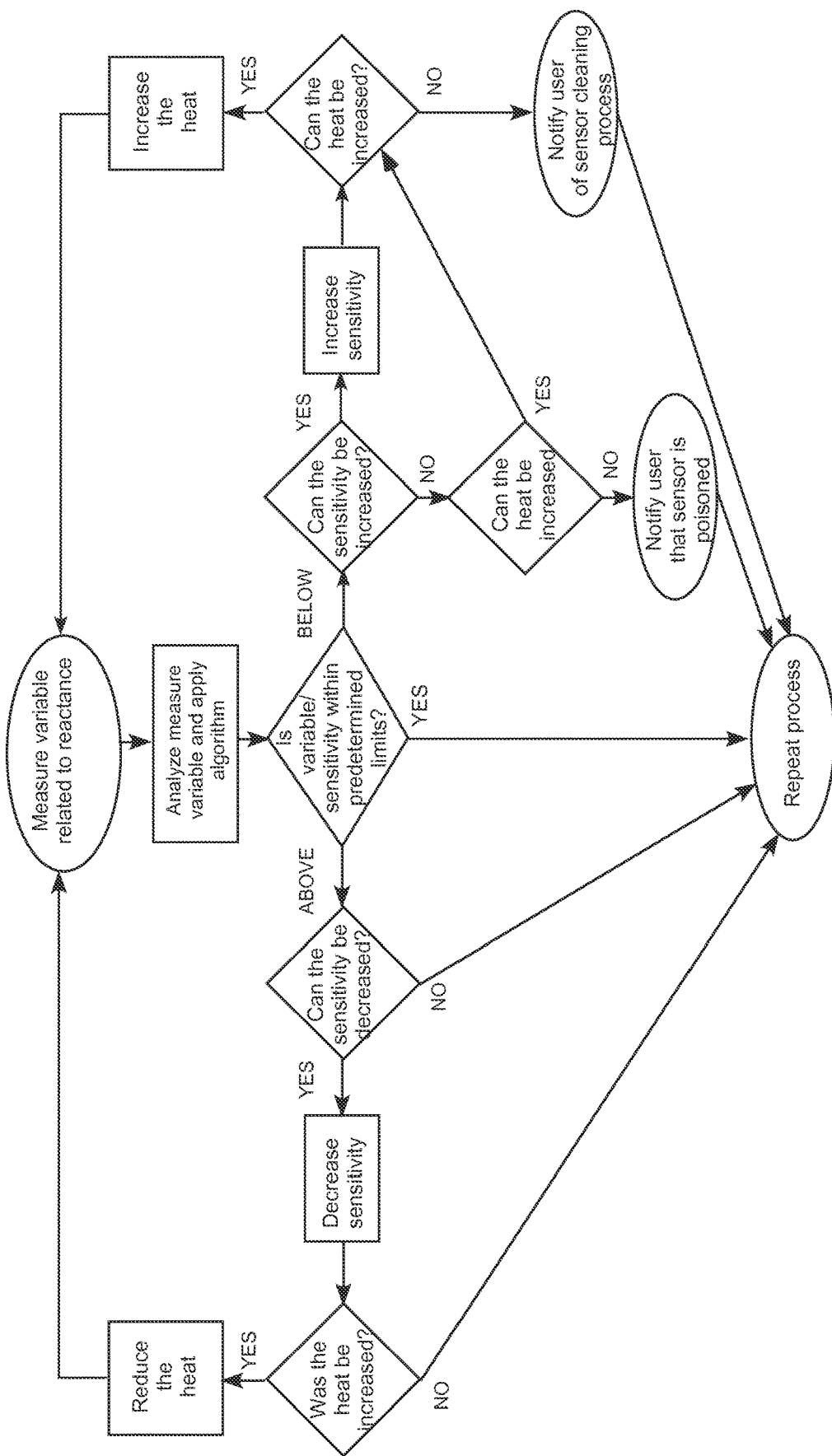
FIG. 7 illustrates an embodiment of a control or interrogation algorithm or procedure of an embodiment of a method or a sensor system hereof.

FIG. 7 illustrates an embodiment of an electronic interrogation or control algorithm or process hereof. In the embodiment of FIG. 7, each time a variable related to reactance is read, it is evaluated. If the variable and/or a correction of sensitivity associated therewith is within normal limits (for example, +/−1% of a predetermined value), no corrections occur and the sequence repeats. If a nonconforming result is obtained (that is, the variable and/or correction is not within normal limits), different actions are taken depending upon whether sensitivity should be increased or decreased, which is dependent upon the measured variable. If the measured variable results in a need to increase the sensitivity (for example, associated with contamination of the sensing element), the algorithm will determine if the increase is within normal limits, and do so. If the increase is within normal limits, the system will attempt to increase the heat to burn off any inhibitors, and the user may, for example, be alerted that this "burn-off" or cleaning process is taking place. If the maximum thermal limit has already been applied, and the maximum correction has also been applied, then the user may, for example, be alerted that the sensing element has been poisoned. If the measured variable results in the need to decrease the sensitivity, the algorithm will determine if the decrease is within normal limits, and do so. If the decrease is within normal limits, the system will check to see if heat had been previously applied to attempt to burn off an inhibitor. If heat had been applied, the heat will be reduced. This control algorithm or a similar algorithm hereof may, for example, be an automated procedure carried out via the control system without the need for user intervention. The control algorithm may, for example, be embodied in software stored within memory system 198 and executed by processor 196 of control system 194. In a number of embodiments, the combustible gas sensor is operative to detect the combustible gas analyte during the execution of the electronic interrogation, control algorithm or process.

The devices, systems and/or methods described herein can be used in connection with a variety of types of combustible gas sensors. Existing combustible gas sensors designs are readily modified to include a device or system hereof for measuring an impedance variable related to reactance of one or more sensing elements thereof. For example, such devices, systems and/or methods can be used in connection with Micro-Electro-Mechanical Systems (MEMS), thin/thick film system, or other suitable micro- or nanotechnology systems such as, for example, described in U.S. Pat. No. 5,599,584 and/or U.S. Pat. No. 6,705,152.

The foregoing description and accompanying drawings set forth embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A combustible gas sensor for detecting a combustible analyte gas, comprising: a first sensing element comprising a first conductive element in electrical connection with an electronic circuitry, a first support structure in operative connection with the first conductive element, a catalytic structure comprising a metallic catalyst supported on the first support structure for catalyzing a reaction of the combustible analyte gas, the electronic circuitry comprising a bridge circuit to measure a change in resistance of the first sensing element over time, the electronic circuitry determining a concentration of the combustible analyte gas from the change in resistance of the first sensing element, the electronic circuitry further comprising a circuit to vary a voltage or a current applied to the first sensing element in an oscillatory manner and to measure an electrical property of the first sensing element which varies with variation in reactance of the first sensing element, changes in the electrical property of the first sensing element being measured over time, independently of measuring the resistance of the first sensing element, and without applying the combustible analyte gas or a simulant therefor, the electronic circuitry monitoring for change in the electronic property over time for a given bias potential, wherein a measured change in the electrical property for a given bias potential above a threshold value is determined to be indicative of a change in the catalytic structure via contamination from a foreign material.

2. The combustible gas sensor of claim 1 wherein the first conductive element passes through at least a portion of the first support structure.

3. The combustible gas sensor of claim 1 further comprising a compensating element comprising a second conductive element in electrical connection with the bridge circuit of the electronic circuitry and a second support structure in operative connection with the second conductive element, the compensating element being substantially non-reactive with the combustible analyte gas at a temperature of operation of the compensating element.

4. The combustible gas sensor of claim 1 wherein the first support structure comprises a porous, electrically insulating material.

5. The combustible gas sensor of claim 4 wherein the first support structure comprises a porous refractory material.

6. The combustible gas sensor of claim 1 further comprising a control system in communicative connection with the electronic circuitry.

7. The combustible gas sensor of claim 6 wherein the control system is adapted to alter the output of the combustible gas sensor based on the measured change in the electrical property of the first sensing element.

8. The combustible gas sensor of claim 6 wherein the control system is adapted to provide information to a user regarding the measured change in the electrical property of the first sensing element.

9. The combustible gas sensor of claim 6 wherein the control system is adapted to increase the temperature of the first sensing element based upon the measured change in the electrical property of the first sensing element to attempt to burn off the foreign material.

10. The combustible gas sensor of claim 9 wherein the control system is adapted to provide an indication to a user via a display system or via an alarm system of the combustible gas sensor in operative connection with the control system in the case that the measured electrical property of the first sensing element fails to return to a predetermined threshold as a result of the increase in temperature.

11. The combustible gas sensor of claim 1 wherein the electrical property of the first sensing element is one of an impedance, a reactance, a resonant frequency, a frequency dependent variable, an inductance, or a capacitance, a reactive component of inductance, or a reactive component of capacitance, of the first sensing element.

12. The combustible gas sensor of claim 1 wherein the combustible gas sensor is operative to detect the combustible analyte gas while the electrical property of the first sensing element is measured.

13. A method of operating a combustible gas sensor for detecting a combustible analyte gas comprising a first sensing element comprising a first conductive element in electrical connection with an electronic circuitry, a first support structure in operative connection with the first conductive element, a catalytic structure comprising a metallic catalyst supported on the first support structure for catalyzing a reaction of the combustible analyte gas, the method comprising: monitoring for a change in a concentration of the combustible analyte gas by measuring a resistance of the first sensing element over time, varying a voltage or a current applied to the first sensing element in an oscillatory manner, measuring an electrical property of the first sensing element which varies with variation in reactance of the first sensing element over time, independently of monitoring for the change in the concentration of the combustible analyte gas, and without applying the combustible analyte gas or a simulant therefor; and at least one of (i) providing information to a user regarding a change in the catalytic structure of the first sensing element based on changes in the electrical property of the first sensing element or (ii) increasing the temperature of the first sensing element based upon changes in the electrical property to attempt to burn off a foreign material.

14. A method of interrogating a first sensing element comprising a first conductive element in electrical connection with an electronic circuitry, a support structure in operative connection with the first conductive element, and a catalyst structure comprising a metallic catalyst supported on the support structure for catalyzing a reaction of a combustible gas analyte, the method comprising: varying a voltage or a current applied to the first sensing element in an oscillatory manner, measuring an electrical property of the first sensing element which varies with variation in reactance of the sensing element over time independently of monitoring for a change in a concentration of the combustible gas analyte and without applying the combustible gas analyte or a simulant therefor and monitoring for change in the electronic property over time for a given bias potential, wherein a measured change in the electrical property for a given bias potential above a threshold value is determined to be indicative of a change in the catalytic structure via contamination from a foreign material.

15. A method of operating a combustible gas sensor for detecting a combustible analyte gas comprising a first sensing element comprising a first conductive element in electrical connection with an electronic circuitry, a first support structure in operative connection with the first conductive element, a catalyst structure comprising a metallic catalyst supported on the first support structure for catalyzing a reaction of the combustible analyte gas, and a control system in operative connection with the first sensing element, the method comprising: monitoring for a change in a concentration of the combustible analyte gas by monitoring for a change in resistance of the first sensing element and electronically interrogating, the sensing element via the control system independently of monitoring for the change in the concentration of the combustible gas analyte and without applying the combustible analyte gas or a simulant therefor to the first sensing element by varying a voltage or a current applied to the first sensing element in an oscillatory manner and measuring an electrical property of the first sensing element which varies with variation in reactance of the sensing element over time and increasing the temperature of the first sensing element via the control system upon determining a threshold value of change in the measured electrical property to attempt to burn off any foreign material.

16. The method of claim 15 further comprising repeating the electronic interrogation to determine whether the measured electrical property returns to the threshold value.

17. The method of claim 16 further comprising providing an indication to a user via a display system or via an alarm system of a failure the measured electrical property fails to return to the threshold value.

18. The method of claim 16 wherein the measured electrical property of the first sensing element is an impedance, reactance, a resonant frequency, a frequency dependent variable, an inductance, or a capacitance, a reactive component of inductance, or a reactive component of capacitance, of the first sensing element.

* * * * *

UNITED STATES PATENT AND TRADEMARK OFFICE
CERTIFICATE OF CORRECTION

| | |
|---|---|
| PATENT NO. | : 10,578,573 B2 |
| APPLICATION NO. | : 13/795452 |
| DATED | : March 3, 2020 |
| INVENTOR(S) | : Mark Flori Zanella, Sr. |

It is certified that error appears in the above-identified patent and that said Letters Patent is hereby corrected as shown below:

In the Specification
Column 6, Line 56, insert a --.-- between "150" and "Active".
Column 6, Line 62, delete "70" and insert --170--.
Column 7, Line 36, delete "140" and insert --130--.
Column 9, Line 58, delete "to related" and insert --to relate--.
In the Claims
Column 14, Claim 17, Line 12, delete "a failure the measured electrical property" and insert --a failure if the measured electrical property--.

Signed and Sealed this
Fifth Day of May, 2020

Andrei Iancu
*Director of the United States Patent and Trademark Office*